(12) United States Patent
Takehara

(10) Patent No.: US 10,775,353 B2
(45) Date of Patent: Sep. 15, 2020

(54) METHOD FOR DETERMINING DISSOLVED-HYDROGEN CONCENTRATION

(71) Applicant: Aqua Bank CO., LTD., Osaka (JP)

(72) Inventor: Takashi Takehara, Osaka (JP)

(73) Assignee: Aqua Bank CO., LTD., Osaka (JP)

( * ) Notice: Subject to any disclaimer, the term of this patent is extended or adjusted under 35 U.S.C. 154(b) by 848 days.

(21) Appl. No.: 14/760,448

(22) PCT Filed: Jan. 14, 2014

(86) PCT No.: PCT/JP2014/050434
§ 371 (c)(1),
(2) Date: Sep. 16, 2015

(87) PCT Pub. No.: WO2014/109410
PCT Pub. Date: Jul. 17, 2014

(65) Prior Publication Data
US 2016/0003785 A1    Jan. 7, 2016

(30) Foreign Application Priority Data
Jan. 11, 2013   (JP) .................................. 2013-003950

(51) Int. Cl.
*G01N 30/66*   (2006.01)
*G01N 30/12*   (2006.01)
(Continued)

(52) U.S. Cl.
CPC ............. *G01N 30/66* (2013.01); *G01N 30/12* (2013.01); *G01N 33/18* (2013.01); *G01N 33/182* (2013.01);
(Continued)

(58) Field of Classification Search
CPC .................................................... G01N 33/18
(Continued)

(56) References Cited

U.S. PATENT DOCUMENTS 3,097,518 A * 7/1963 Taylor et al. ........ G01N 27/185
                                                      73/23.4
3,922,904 A * 12/1975 Williams ................. G01N 7/00
                                                      73/19.1
(Continued)

FOREIGN PATENT DOCUMENTS

JP        59-114461 A    7/1984
JP        2009-008476 A  1/2009
(Continued)

OTHER PUBLICATIONS

Kang et al. Medical Gas Research 2011, 1:11.*

*Primary Examiner* — Nathaniel J Kolb
(74) *Attorney, Agent, or Firm* — Novick, Kim & Lee, PLLC; Jae Youn Kim

(57) ABSTRACT

The present invention is configured of: a gas control step in which a carrier gas that differs in thermal conductivity from hydrogen by a given value is chosen, and the flow rate thereof is controlled; a sample introduction step in which an aqueous solution sample is prepared and introduced into the carrier gas serving as a mobile phase and which is characterized in that the preparation of an aqueous solution sample comprises injecting an aqueous solution sample into a vessel, the inside of which is kept vacuum, to thereby conduct gas-liquid separation and collecting the gas-phase portion as a sample to be introduced; a separation step in which the hydrogen is separated from the aqueous solution sample on the basis of an adsorption/distribution equilibrium between the aqueous solution sample introduced into the mobile phase and the fixed phase of the column; a detection step; and a data processing step.

2 Claims, 1 Drawing Sheet

(51) Int. Cl.
*G01N 33/18* (2006.01)
*G01N 30/88* (2006.01)
*G01N 30/02* (2006.01)

(52) U.S. Cl.
CPC ............... *G01N 2030/025* (2013.01); *G01N 2030/8859* (2013.01)

(58) Field of Classification Search
USPC .................................................. 96/193, 413
See application file for complete search history.

(56) References Cited

U.S. PATENT DOCUMENTS

| | | | |
|---|---|---|---|
| 5,777,214 A * | 7/1998 | Thompson | G01N 1/34 73/19.12 |
| 5,979,554 A * | 11/1999 | Mancini | B01D 19/0036 166/267 |

FOREIGN PATENT DOCUMENTS

| | | | |
|---|---|---|---|
| JP | 2010-249651 A | 11/2010 | |
| JP | 5004112 B1 | 8/2012 | |

* cited by examiner

METHOD FOR DETERMINING DISSOLVED-HYDROGEN CONCENTRATION

TECHNICAL FIELD

The present invention relates to a method of measuring the concentration of hydrogen dissolved in an aqueous solution using gas chromatography.

BACKGROUND ART

In recent years, hydrogen has been found to have the effect of removing active oxygen, which is thought to cause aging and cancer. It is also reported that, when drinking water containing hydrogen, it is possible to remove active oxygen in the body and to remedy health impairments, such as allergic diseases and digestive diseases. The use of water having hydrogen dissolved therein (hereinafter, referred to as hydrogen water) as a drink in consideration of the fact that hydrogen has the effect of removing active oxygen as described above has attracted considerable attention. In fact, the market for hydrogen water for drinking has quickly expanded.

It is generally thought that, when the concentration of hydrogen contained in hydrogen water is high, the hydrogen water has the effect of removing active oxygen. For this reason, the amount of hydrogen that is contained in hydrogen water is important in showing the effect of the hydrogen water. Consequently, it is considerably important to know the concentration of hydrogen in hydrogen water, i.e. the concentration of hydrogen molecules contained in an aqueous solution (hereinafter, referred to as dissolved hydrogen).

In general, however, no clear criterion is prescribed for a method of measuring the concentration of dissolved hydrogen (such a criterion is not prescribed even in, for example, JIS standards). In addition, in a conventional method of measuring the concentration of dissolved hydrogen, the concentration of dissolved hydrogen is generally calculated on the basis of oxidation-reduction potential (for example, Patent Document 1). Consequently, all materials having an influence on oxidation and reduction are measured, and therefore it is not clear whether or not the concentration of only hydrogen dissolved in an aqueous solution is appropriately displayed.

RELATED ART DOCUMENT

Patent Document

Patent Document 1: Japanese Patent Application Publication No. 2009-8476

DISCLOSURE

Technical Problem

Conventionally, as disclosed in Patent Document 1, the concentration of dissolved hydrogen is generally measured on the basis of oxidation-reduction potential. Oxidation-reduction potential is an index showing the oxidation and reduction power of an aqueous solution. For this reason, when measuring on the basis of oxidation-reduction potential, the sum of the oxidation power and reduction power of all materials contained in an aqueous solution is measured. In this measurement method, therefore, it is not clear whether or not the concentration of only hydrogen dissolved in an aqueous solution is measured. As a result, it is not possible to accurately measure the concentration of hydrogen dissolved in an aqueous solution.

The present invention has been made in view of the above problems, and it is an object of the present invention to provide a method of separating hydrogen from an aqueous solution using gas chromatography and measuring the concentration of only the separated hydrogen. It is another object of the present invention to provide a method of increasing measurement sensitivity using a predetermined carrier gas and thermal conductivity detector (TCD) to accurately measure the concentration of hydrogen dissolved in an aqueous solution.

Technical Solution

A method of measuring the concentration of hydrogen dissolved in an aqueous solution according to the present invention is a method using gas chromatography including a gas control process for selecting a carrier gas having a predetermined difference in thermal conductivity from hydrogen and controlling a flow rate of the carrier gas, a sample introduction process for preparing an aqueous solution sample and introducing the prepared aqueous solution sample into the carrier gas, which functions as a mobile phase, a separation process for separating hydrogen from the aqueous solution sample on the basis of equilibrium in adsorption and distribution between the aqueous solution sample introduced in the mobile phase and a stationary phase of a column, a detection process for detecting the separated hydrogen using a thermal conductivity detector (TCD), and a data processing process for processing the detected data.

TABLE 1

| Gas | Thermal conductivity (0° C.) $10^{-5}$ cal/sec * cm * ° C. |
|---|---|
| Helium (He) | 34.31 |
| Hydrogen ($H_2$) | 41.81 |
| Nitrogen ($N_2$) | 5.81 |
| Carbon monoxide (CO) | 5.43 |
| Argon (Ar) | 3.88 |
| Oxygen ($O_2$) | 5.70 |
| Carbon dioxide ($CO_2$) | 3.39 |
| Methane ($CH_4$) | 7.20 |
| Ethane ($C_2H_6$) | 4.31 |
| Propane ($C_3H_8$) | 3.60 |

In the detection process, a thermal conductivity detector (TCD), which converts the difference in thermal conductivity between hydrogen and the carrier gas into a voltage difference to detect the difference in thermal conductivity, is used. In the gas control process, therefore, a carrier gas having a predetermined difference in thermal conductivity from hydrogen is selected, whereby it is possible to improve sensitivity in detection of hydrogen. As can be seen from thermal conductivities shown in Table 1, hydrogen, which has no difference in thermal conductivity from hydrogen, and helium (34.31), which has a little difference in thermal conductivity from hydrogen, are not preferable as the carrier gas. On the other hand, nitrogen, carbon monoxide, argon, oxygen, carbon dioxide, methane, ethane, and propane, which have a great difference in thermal conductivity from hydrogen, are preferable as the carrier gas.

In the sample introduction process, the preparation of the aqueous solution sample includes injecting a desired amount of the aqueous solution sample into a vessel, the inside of which is maintained in a vacuum state, to thereby perform gas and liquid separation, and collecting a gas-phase portion as a sample to be introduced using a vacuum gas sampling bottle method.

In the vacuum gas sampling bottle method, which is used to prepare an aqueous solution, it is possible to introduce an aqueous solution sample as a gas having a lower density than a liquid, whereby it is possible to perform measurement using a smaller amount of the aqueous solution sample than when introducing the aqueous solution sample into a carrier gas, which is a gas-phase portion as a liquid. Furthermore, the dissolved gas is concentrated from the aqueous solution, whereby the gas and liquid are separated. Consequently, it is possible to collect a gas having a high concentration as a sample to be introduced. Since it is possible to perform measurement using a small amount of the aqueous solution sample, it is possible to improve separability between hydrogen and another material using gas chromatography. In addition, the time necessary to detect the separated hydrogen is reduced, and it is possible to collect a gas having a high concentration. Consequently, it is possible to detect hydrogen at high sensitivity, even using a small amount of the aqueous solution sample.

In addition, in the method of measuring the concentration of dissolved hydrogen according to the present invention, the gas control process includes selecting nitrogen as the carrier gas. Nitrogen is preferable in that nitrogen has a great difference in thermal conductivity from hydrogen, whereby it is possible to improve sensitivity in detection, as shown in Table 1, and in that nitrogen is cheaper than other gases, and can be handled with high safety, whereby it is possible to reduce the costs incurred in measurement.

Furthermore, the method of measuring the concentration of dissolved hydrogen according to the present invention may be used as a method of measuring the concentration of hydrogen dissolved in an aqueous solution for drinking. The aqueous solution for drinking is preferable in that the aqueous solution for drinking has few impurities, and therefore it is possible to reduce the time necessary to separate hydrogen from other materials in the separation process, whereby it is possible to reduce the measurement time. In addition, the aqueous solution for drinking is preferable in that the aqueous solution for drinking does not contain inorganic salts or inorganic acids, and therefore it is possible to prevent rapid deterioration due to inorganic salts or inorganic acids in the separation process during measurement, whereby it is possible to reduce costs.

Advantageous Effects

According to the present invention, a carrier gas having a predetermined difference in thermal conductivity from hydrogen is selected, and a thermal conductivity detector (TCD) is used. Consequently, it is possible to greatly improve sensitivity in detection of hydrogen. Next, hydrogen is separated from other gases, and is then measured, using gas chromatography. Consequently, it is possible to accurately measure the concentration of dissolved hydrogen. Additionally, a vacuum gas sampling bottle method is used. Consequently, it is possible to improve sensitivity in detection of hydrogen and to reduce the measurement time.

In addition, according to the present invention, nitrogen is selected as the carrier gas. Consequently, it is possible to further improve sensitivity in detection of hydrogen and to reduce cost.

Furthermore, according to the present invention, an aqueous solution for drinking is measured. Consequently, it is possible to further reduce measurement time and to reduce the costs incurred in measurement.

BEST MODE

Hereinafter, an embodiment of the present invention will be described with reference to the accompanying drawings.

Figure 1:
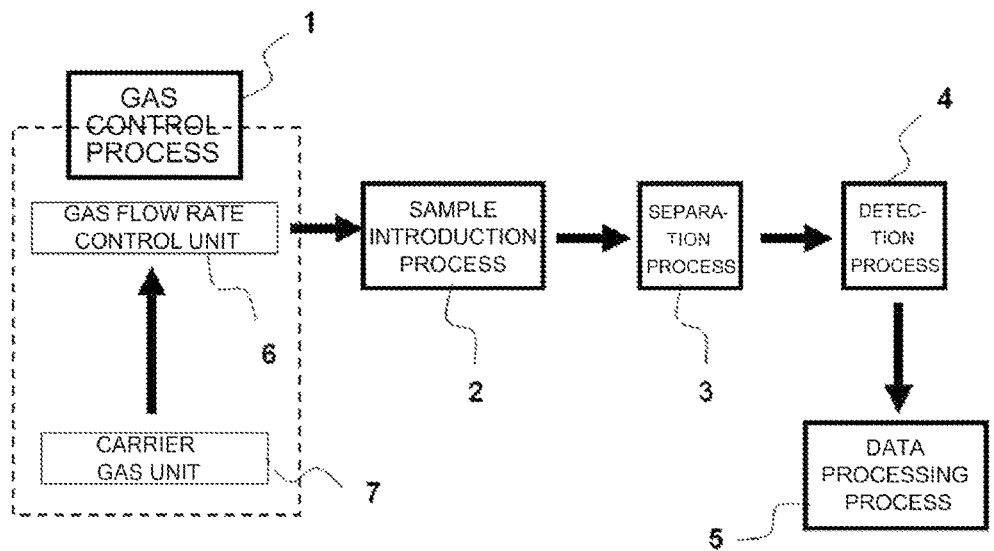
FIG. 1 is a typical view showing all processes of a measurement method according to the present invention.

FIG. 1 is a typical view showing all processes of gas chromatography according to the present invention. Reference numeral 1 indicates a gas control process, 2 indicates a sample introduction process, 3 indicates a separation process, 4 indicates a detection process, and 5 indicates a data processing process.

The gas control process 1 includes a carrier gas unit 7 and a gas flow rate control unit 6. In the gas control process 1, a carrier gas is discharged from the carrier gas unit 7, and a flow rate of the discharged carrier gas is controlled by the gas flow rate control unit 6. The carrier gas, the flow rate of which is controlled, functions as a mobile phase. A carrier gas that is selected by the carrier gas unit 7 is used. However, a thermal conductivity detector (TCD), which converts the difference in thermal conductivity between hydrogen and the carrier gas into a voltage difference to detect the difference in thermal conductivity, is used in the detection process 4. For this reason, a gas having a great difference in thermal conductivity from hydrogen, which is a target to be measured, is preferably selected as the carrier gas.

A gas having a great difference in thermal conductivity from hydrogen, which is a target to be measured, is preferably selected as the carrier gas. When hydrogen having a thermal conductivity of 41.81 (in units of $10^{-5}$ cal/sec*cm*° C.) is measured at a temperature of 0° C., therefore, hydrogen, which has no difference in thermal conductivity from hydrogen, and helium (34.31), which has little difference in thermal conductivity from hydrogen, are not preferable as the carrier gas, as can be seen from Table 1 showing thermal conductivities. On the other hand, nitrogen (5.81), carbon monoxide (5.43), argon (3.88), oxygen (5.70), carbon dioxide (3.39), methane (7.20), ethane (4.31), and propane (3.60), which have a great difference in thermal conductivity from hydrogen, are preferable as the carrier gas. In addition, nitrogen has a great difference in thermal conductivity from hydrogen, is cheaper than the other gases, and can be handled with high safety. Consequently, nitrogen is particularly preferable.

In the sample introduction process 2, an aqueous solution sample is introduced into the mobile phase formed in the gas control process 1. The introduced aqueous solution sample is carried to the separation process 3 by the mobile phase. In the sample introduction process 2, the aqueous solution sample is prepared using a vacuum gas sampling bottle method. The aqueous solution sample prepared using the vacuum gas sampling bottle method is introduced into the mobile phase formed in the gas control process 1, and the introduced aqueous solution sample is carried to the separation process 3 by the mobile phase. In the vacuum gas sampling bottle method, a small amount of high-concentration gas may be used as a sample that is introduced, whereby it is possible to improve sensitivity in detection of hydrogen and to reduce the measurement time. The vacuum gas sampling bottle method will hereinafter be described with reference to FIG. 2.

The separation process 3 is a process in which the mobile phase formed in the gas control process, into which the aqueous solution sample is introduced by the sample introduction process 3, is introduced into to a column having a stationary phase. Hydrogen is separated from the other materials in the aqueous solution sample on the basis of equilibrium in adsorption and distribution between the stationary phase and the aqueous solution sample in the mobile phase. The separated hydrogen is carried to the detection process 4 by the mobile phase. Since hydrogen is separated from the aqueous solution sample, it is possible to accurately measure only the hydrogen dissolved in the aqueous solution.

In the detection process 4, hydrogen, which is separated in the separation process 3 and is then carried to the detection process 4, is detected. The detected data are processed by the data processing process 5. A thermal conductivity detector (TCD) is used as a detector. The thermal conductivity detector detects the difference in thermal conductivity between the gas and a carrier gas as a voltage difference. Consequently, a carrier gas having a predetermined difference in thermal conductivity from hydrogen is selected by the carrier gas unit 7 of the gas control process 1, whereby it is possible to detect hydrogen at high sensitivity.

In the data processing process 5, the detected data are processed. Data processing is performed for the area or the height of a detected peak, and the concentration of hydrogen dissolved in the aqueous solution sample is calculated from a ratio of the weight of the aqueous solution sample introduced in the sample introduction process 2.

Figure 2:
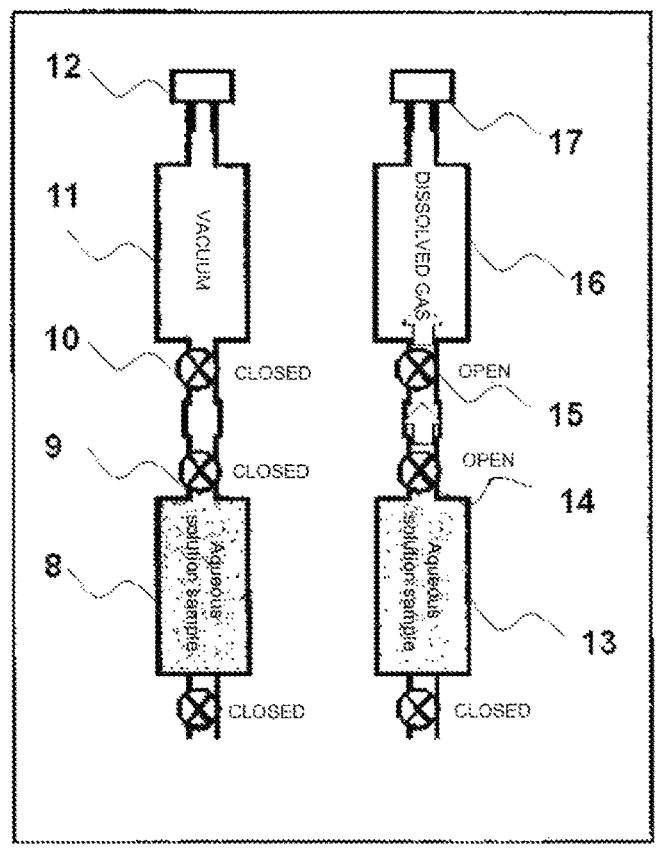
FIG. 2 is a typical view showing a gas and liquid separation process in a case in which an aqueous solution sample is prepared using a vacuum gas sampling bottle method in a sample introduction process 2.

FIG. 2 is a typical view showing a gas and liquid separation process in a case in which the aqueous solution sample is prepared using a vacuum gas sampling bottle method in the sample introduction process 2. Reference numeral 8 indicates the aqueous solution sample, 9 and 10 indicate valves interconnecting the aqueous solution sample 8 and a vacuum gas sampling bottle, 11 indicates the vacuum gas sampling bottle, and 12 indicates a septum unit. 13 indicates an aqueous solution sample after opening of the valves 9 and 10, 14 and 15 indicate valves after opening of the valves 9 and 10, 16 indicates a vacuum gas sampling bottle after opening of the valves 9 and 10, and 17 indicates a septum unit after opening of the valves 9 and 10.

Before the aqueous solution sample is introduced in the sample introduction process 2, gas and liquid in the aqueous solution sample are separated from each other using the vacuum gas sampling bottle method. The aqueous solution sample 8 is connected to the vacuum gas sampling bottle via the valves 9 and 10. When the valves 8 and 9 are opened, the aqueous solution sample 13 is introduced into the vacuum gas sampling bottle 16 via the valves 14 and 15, and gas and liquid in the aqueous solution sample are separated from each other, whereby a dissolved gas is obtained. Subsequently, the vessel is disposed such that the septum unit 17 is located at the upper side, ion exchanged water is introduced through a collection port of the vessel so as to maintain the atmospheric pressure, and a gas-tight syringe is stuck to the septum unit 17 of the vessel, which is located at the upper side, to extract a dissolved gas (gas-phase portion). In the sample introduction process 2, the extracted and collected gas-phase portion is introduced into the mobile phase formed in the gas control process 1. Since a small amount of high-concentration gas can be used as a sample that is introduced, it is possible to improve sensitivity in detection of hydrogen and to reduce the measurement time.

EXAMPLE 1

According to the measuring method based on gas chromatography of the present invention, the concentration of dissolved hydrogen was measured using the vacuum gas sampling bottle method in the sample introduction process 2. The amount of an aqueous solution sample was obtained from the difference in weight between the vessel before gas and liquid were separated from each other and the empty weight of the vessel, and the amount of gas was obtained using specific gravity of water from the difference in weight between the vessel at a full water level and the vessel immediately before the gas concentration was measured. The density of water at the corresponding temperature was obtained from Table 1 in the attachment of JIS K0061 (2001), and the specific gravity of water was calculated from a ratio of the obtained density of water to 0.99997 (the density of water at 4° C.).

Tap water and water obtained by allowing tap water to pass through an 'AquaBank' water server (hereinafter, referred to as a server) were used as the aqueous solution sample. In addition to the measurement according to the present invention, the concentration of dissolved hydrogen was also measured using a portable hydrogen meter. The results are shown as follows. The server is configured such that, as water passes through the server, a large amount of hydrogen is contained in the water.

TABLE 2

| Sample name Cold water/Hot water | Tap water before passing | 3 hours after server installation | | 6 hours after server installation | |
| --- | --- | --- | --- | --- | --- |
| | | Cold water | Hot water | Cold water | Hot water |
| Concentration of $H_2$ in water (measured using vacuum bottle) ($\mu gH_2/kgH_2O$ (=ppb)) | <0.6 | 24 | 19 | 35 | 53 |
| Concentration of $H_2$ in water (measured using hydrogen meter) (ppb) | 0 | 332 | 190 | 296 | 331 |
| Remarks | | | | | |

| Sample name Cold water/Hot water | 24 hours after server installation | | 24 hours after server installation + leaving at room temperature for 1 hour | |
| --- | --- | --- | --- | --- |
| | Cold water | Hot water | Cold water | Hot water |
| Concentration of $H_2$ in water (measured using vacuum bottle) ($\mu gH_2/kgH_2O$ (=ppb)) | 120 | 100 | 120 | 60 |
| Concentration of $H_2$ in water (measured using hydrogen meter) (ppb) | 501 | 300 | 424 | 476 |
| Remarks | | | | |

TABLE 2-continued

| Sample name | 24 hours after server installation + leaving at room temperature for 3 hours | | 24 hours after server installation + leaving at room temperature for 6 hours | |
|---|---|---|---|---|
| Cold water/Hot water | Cold water | Hot water | Cold water | Hot water |
| Concentration of $H_2$ in water (measured using vacuum bottle) ($\mu gH_2/kgH_2O$ (=ppb)) | 110 | 17 | 110 | 86 |
| Concentration of $H_2$ in water (measured using hydrogen meter) (ppb) | 418 | 322 | 351 | 360 |
| Remarks | | | | |

In Table 2, 'measurement using vacuum bottle' means the measurement according to the present invention, and 'measurement using hydrogen meter' means the measurement using the portable hydrogen meter. 'Tap water before passing' means the tap water that has not passed through the server, 'server installation' means that the aqueous solution sample has passed through the server, '3 hours after server installation' means that the aqueous solution sample has passed through the server for three hours, '+ leaving at room temperature for 1 hour' means that the aqueous solution sample, having passed through the server, was left at the room temperature for one hour.

Referring to the measurement results according to the present invention in order of 'tap water before passage of water', '3 hours after server installation', '6 hours after server installation', and '24 hours after server installation' together with the passage of time of the server installation, the concentration of $H_2$ in water (in units of $\mu gH_2/kgH_2O$ (=ppb, 28° C.)) was less than a detection limit, 24, 35, and 120 for cold water, and was less than the detection limit, 19, 53, and 100 for hot water. In contrast, the measurement results using the portable hydrogen meter were 0, 332, 296, and 501 for cold water, and were 0, 190, 331, and 300 for hot water. When considering that the concentration of hydrogen dissolved in the aqueous solution increases due to the server installation, the measurement results according to the present invention reveal that it is possible to appropriately measure the concentration of hydrogen dissolved in the aqueous solution, as compared with the measurement results using the portable hydrogen meter.

In addition, referring to the measurement results according to the present invention in order of '24 hours after server installation', '24 hours after server installation+leaving at room temperature for 1 hour', '24 hours after server installation+leaving at room temperature for 3 hours', and '24 hours after server installation+leaving at room temperature for 6 hours' together with the amount of time that the water was left at the room temperature after having passed through the server for 24 hours, the concentration of $H_2$ in water (in units of $\mu gH_2/kgH_2O$(=ppb, 28° C.)) was 120, 120, 110, and 110 for cold water, and was 100, 60, 17, and 86 for hot water. In contrast, the measurement results using the portable hydrogen meter were 501, 424, 418, and 351 for cold water, and were 300, 476, 322, and 360 for hot water. Here, it is considered that the concentration of hydrogen dissolved in the aqueous solution decreases with the passage of time after server installation. The measurement results according to the present invention reveal that it was possible to appropriately measure the concentration of hydrogen dissolved in the aqueous solution, except that the value measured after the lapse of six hours was higher than the value measured after the lapse of three hours. In contrast, the measurement results using the portable hydrogen meter reveal that the value measured after the lapse of six hours was higher than the value measured after the lapse of three hours, and the value measured after the lapse of one hour was higher than the value measured after the lapse of zero hours. Consequently, the measurement results according to the present invention reveal that it is possible to accurately measure the concentration of hydrogen dissolved in the aqueous solution, as compared with the measurement results using the portable hydrogen meter.

EXAMPLE 2

According to the measuring method based on gas chromatography of the present invention, the concentration of dissolved hydrogen was measured using the vacuum gas sampling bottle method in the sample introduction process. The concentration of hydrogen in an aqueous solution sample (gas-phase portion) collected using the vacuum gas sampling bottle method was measured to calculate the concentration of hydrogen in water.

Measurement was performed according to the present invention using pure water and water obtained by bubbling hydrogen gas in pure water for 10 minutes as the aqueous solution sample. The results are shown as follows.

TABLE 3

| | Pure water | Hydrogen gas bubbled water |
|---|---|---|
| Sample water amount g | 194 | 194 |
| Extracted gas amount mL | 2.3 | 2.9 |
| Concentration of hydrogen in gas Vol % | 0.3 | 63 |
| Concentration of hydrogen in water $\mu gH_2/kgH_2O$ (=ppb, 28° C.) | 3 | 760 |

In Table 3, 'hydrogen gas bubbled water' means water obtained by bubbling hydrogen gas in pure water for 10 minutes, 'sample water amount' means the amount of the prepared aqueous solution sample, 'extracted gas amount' means the amount of the aqueous solution sample (gas-phase portion) collected using the vacuum gas sampling bottle method, 'concentration of hydrogen in gas' means the concentration of hydrogen in the aqueous solution sample (gas-phase portion) collected using the vacuum gas sampling bottle method, and 'concentration of hydrogen in water' means the concentration of hydrogen calculated from the concentration of hydrogen in the aqueous solution sample (gas-phase portion) measured according to the present invention, the amount of the aqueous solution sample and the specific gravity of water.

The measurement results according to the present invention reveal that, referring to the concentration of hydrogen in water (in units of $\mu gH_2/kgH_2O$(=ppb, 28° C.)), the concentration of hydrogen in water obtained by bubbling hydrogen gas in pure water for 10 minutes was 760, and the concentration of hydrogen in pure water was 3, and therefore water obtained by bubbling hydrogen gas in pure water for 10 minutes had a higher concentration of dissolved hydrogen than pure water. Since it is thought that the concentration of hydrogen dissolved in water obtained by bubbling hydrogen gas in pure water increases as compared with the concentration of hydrogen dissolved in pure water, it is possible to appropriately measure the concentration of dissolved hydrogen according to the present invention.

INDUSTRUAL APPLICABILITY

The present invention is applicable to the measurement of the concentration of hydrogen dissolved in a solution.

DESCRIPTION OF REFERENCE NUMERALS

1 Gas control process
2 Sample introduction process
3 Separation process
4 Detection process
5 Data processing process
6 Carrier gas unit
7 Gas flow rate control unit
8 Aqueous solution sample
9, 10 Valves
11 Vacuum gas sampling bottle
12 Septum unit
13 Aqueous solution sample after opening of valves 9 and 10
14, 15 Valves after opening of valves 9 and 10
16 Vacuum gas sampling bottle after opening of valves 9 and 10
17 Septum unit after opening of valves 9 and 10

The invention claimed is:

1. A method of measuring a concentration of hydrogen only dissolved in an aqueous solution for drinking using gas chromatography, the method comprising:
   a gas control process for selecting a carrier gas having a predetermined difference in thermal conductivity from hydrogen and controlling a flow rate of the carrier gas;
   a sample introduction process for preparing an aqueous solution sample and introducing the prepared aqueous solution sample into the carrier gas, which functions as a mobile phase, wherein the preparation of the aqueous solution sample comprises injecting a desired amount of the aqueous solution into a vessel, an inside of which is maintained in a vacuum state, to thereby perform gas and liquid separation and collecting a gas-phase portion as the aqueous solution sample to be introduced;
   a separation process for separating hydrogen only from the aqueous solution sample on a basis of equilibrium in adsorption and distribution between the aqueous solution sample introduced in the mobile phase and a stationary phase of a column;
   a detection process for detecting the separated hydrogen only using a thermal conductivity detector; and
   a data processing process for processing the detected data.

2. The method according to claim 1, wherein the gas control process comprises selecting nitrogen as the carrier gas.

* * * * *